(12) United States Patent
Guo et al.

(10) Patent No.: US 8,983,607 B2
(45) Date of Patent: Mar. 17, 2015

(54) METHOD AND APPARATUS FOR PROTECTING A FUNCTION MODE OF A MEDICAL DEVICE

(75) Inventors: Yanmei Guo, Shenzhen (CN); Saixin Zhou, Shenzhen (CN); Min An, Shenzhen (CN); Dazhi Teng, Shenzhen (CN)

(73) Assignee: Shenzhen Mindray Bio-Medical Electronics Co., Ltd, Shenzhen (CH)

( * ) Notice: Subject to any disclaimer, the term of this patent is extended or adjusted under 35 U.S.C. 154(b) by 1095 days.

(21) Appl. No.: 13/008,794

(22) Filed: Jan. 18, 2011

(65) Prior Publication Data

US 2011/0118799 A1 May 19, 2011

Related U.S. Application Data

(62) Division of application No. 11/943,461, filed on Nov. 20, 2007, now Pat. No. 7,873,416.

(30) Foreign Application Priority Data

Dec. 21, 2006 (CN) .......................... 2006 1 0157816

(51) Int. Cl.
*A61N 1/37* (2006.01)
*A61N 1/39* (2006.01)
*A61N 1/372* (2006.01)

(52) U.S. Cl.
CPC ................ *A61N 1/3925* (2013.01); *A61N 1/37* (2013.01); *A61N 1/37247* (2013.01); *A61N 1/3993* (2013.01)
USPC .......................................................... 607/31

(58) Field of Classification Search
CPC .............................. A61N 1/39; A61N 1/3925
USPC .................................................................. 607/5
See application file for complete search history.

(56) References Cited

U.S. PATENT DOCUMENTS

| 6,141,584 | A | * | 10/2000 | Rockwell et al. ................ 607/5 |
| 6,301,501 | B1 | | 10/2001 | Cronin et al. |
| 2002/0111946 | A1 | | 8/2002 | Fallon |
| 2006/0030904 | A1 | | 2/2006 | Quiles |

FOREIGN PATENT DOCUMENTS

| CN | 2590534 Y | 12/2003 |
| CN | 1723057 A | 1/2006 |
| WO | 0027277 A1 | 5/2000 |

* cited by examiner

*Primary Examiner* — Eric D. Bertram
(74) *Attorney, Agent, or Firm* — Kory D. Christensen; Stoel Rives LLP

(57) ABSTRACT

Methods and apparatus for protecting a function mode of a medical device are described. A method may include the steps of: when an operator selects to use a function mode that needs protection in the medical device, presenting the operator information on a specified operation for entering the selected function mode; receiving an operation of the operator; determining whether the received operation of the operator is identical to the specified operation; and starting the selected function mode, if the determining result is confirmative.

6 Claims, 3 Drawing Sheets

METHOD AND APPARATUS FOR PROTECTING A FUNCTION MODE OF A MEDICAL DEVICE

This application is a divisional of U.S. patent application Ser. No. 11/943,461, filed Nov. 20, 2007, now U.S. Pat. No. 7,873,416.

TECHNICAL FIELD

This invention relates to the medical field, and in particular, to a method and apparatus for protecting the function mode of a medical device.

BACKGROUND ART

A defibrillator is a medical device that is not used frequently, and generally includes functions of defibrillation, pacing, monitoring and so on. The defibrillation can be divided into functions of asynchronous defibrillation, synchronous defibrillation, automatic external fibrillation and the like.

Since the defibrillator also has a parameter monitoring function, it's often used as a monitor. This brings in a problem that when the defibrillator is used as a monitor in a sickroom, the medical staff may be not by the side and then there exists the possibility that a non-medical staff will operates the defibrillator. However, some of the functions of the defibrillator, such as defibrillating, pacing and AED functions, are risky, which may bring a life risk to patients. Therefore, it's required to perform certain kind of conformation when performing these operations, so as to efficiently reduce the risks caused by the use and the misoperation of unauthorized persons.

Among those defibrillators/monitors in the markets, one kind has no corresponding protection and an operator can enter defibrillating or pacing mode of the defibrillator/monitor directly; another kind can be set by a user to choose to be unprotected or with password protection, while an operator is required to input corresponding password when entering those modes. But the requirement to set password protection makes the medical staff very easily to forget the password. Especially when in emergency such as saving a life, the medical staffs are more easily to go into panic. Thus this delays the rescue, and even no effective rescuing measure could be made, causing a patient to die.

SUMMARY OF THE INVENTION

An object of the invention is to address the above technical problems by providing a method and apparatus for protecting a function mode of a medical device, which not only efficiently protects the function modes of the medical device and makes it not to be operated arbitrarily, but also facilitates the use of an operator.

In order to achieve the object, the invention provides a method for protecting a function mode of a medical device, comprising steps of:

when an operator selects to use a function mode that needs protection in the medical device, presenting the operator information on a specified operation for entering the selected function mode;

receiving an operation of the operator;

determining whether the received operation of the operator is identical to the specified operation; and starting the selected function mode, if the determining result is confirmative.

In order to achieve the object, the invention provides an apparatus for protecting a function mode of a medical device, comprising:

a presenting unit, for when an operator selects to use a function mode that needs protection in the medical device, presenting the operator information on a specified operation for entering the selected function mode;

a receiving unit, for receiving an operation of the operator;

a determining unit, for determining whether the received operation of the operator is identical to the specified operation; and a starting unit, for starting the selected function mode when the determining result is confirmative.

BRIEF DESCRIPTION OF THE DRAWING

The features and advantages of this invention will be discussed in conjunction with the accompanying drawings, wherein.

BEST MODE OF CARRYING OUT THE INVENTION

The main idea of this invention is: when an operator selects to use a function mode that needs protection in the medical device, information on a specified operation for entering the selected function mode is presented to the operator; then when receiving an operation of the operator, whether the received operation of the operator is identical to the specified operation is determined; finally, the selected function mode is started, if the determination result is confirmative.

Hereafter, a defibrillator/monitor is taken as an exemplary medical device to describe the method and apparatus for protecting a function mode of a medical device according to the invention in conjunction with the accompanying drawings.

Figure 1:
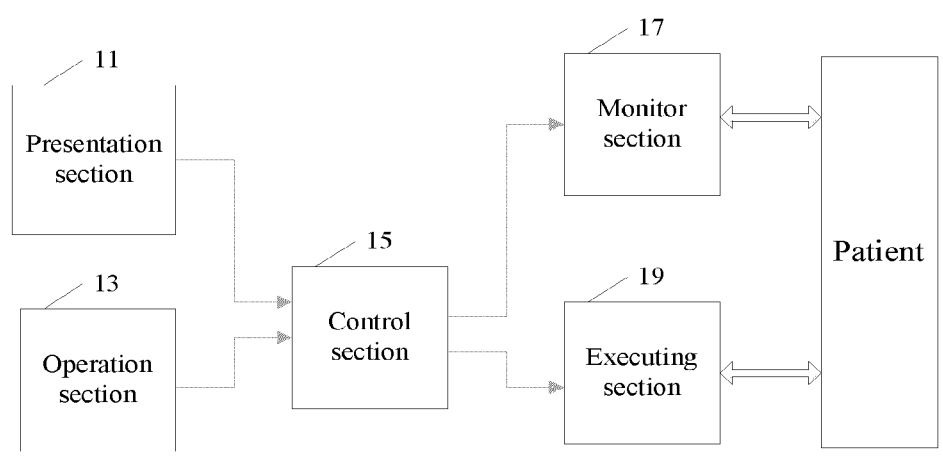
FIG. 1 is a block diagram of the structure of a defibrillator/monitor according to an embodiment of the invention.

FIG. 1 shows a block diagram of the structure of a defibrillator/monitor according to an embodiment of the invention. As shown in FIG. 1, a defibrillator/monitor 10 comprises a presentation section 11, an operation section 13, a control section 15, a monitor section 17 and an executing section 19. Besides performing conventional operations to control the presentation section 11, the operation section 13, the monitor section 17 and an executing section 19, when an operator selects to use a function mode that needs protection in the medical device, the control section 13 also controls the presentation section 11 to present the operator information on a specified operation for entering the selected function mode and information on an alarm, and when the operator performs a corresponding operation via the operation section 13, determines whether the operator's operation received by the operation section 13 is identical to the specified operation, and when the two operations are identical, controls the executing section 19 to start the selected function mode.

Figure 2:
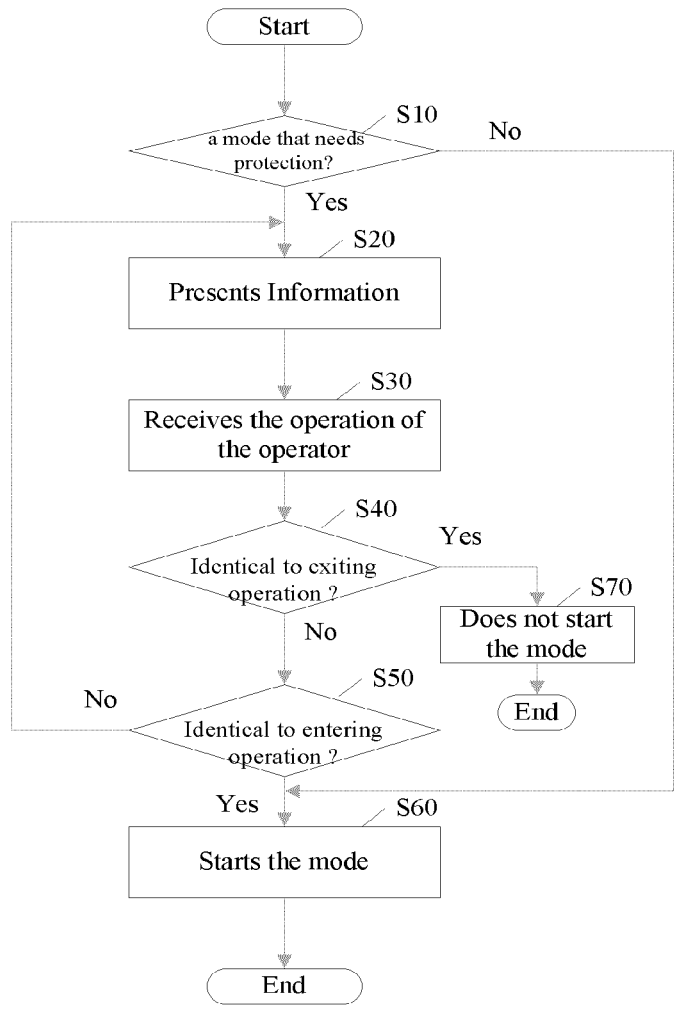
FIG. 2 is a flow chart of a method for protecting a function mode of a defibrillator/monitor according to an embodiment of the invention.

FIG. 2 shows a flow chart of a method for protecting a function mode of a defibrillator/monitor according to an embodiment of the invention. As shown in FIG. 2, at step S10, when the operation section 13 of a defibrillator/monitor 10 receives a signal for selecting a function mode from an operator, the control section 15 determines whether the function mode selected by the operator belongs to the functions that need protection according to the received selecting signal. In this embodiment, the functions that need protection are the function modes with high risks, such as defibrillation, pacing and AED, etc.

When the determining result is no, the procedure proceeds to step S60 at which the control section 15 starts the selected function mode.

When the determining result is yes, at step S20, the presentation section 11 presents the operator information on the specified key operation for entering or exiting the selected function mode and information on an alarm. In this embodiment, the specified key operation is an operation of a single key or a combined operation of two keys or more than two keys. The two keys or more than two keys may be adjacent keys, but they are preferred not adjacent, in order to avoid misoperation. The combined operation of two keys or more than two keys may be that these keys are pressed simultaneously or that these keys are pressed in sequence.

For instance, when the operator selects the defibrillating mode and the defibrillating mode is a function that needs protection, the control section 15 sends the presentation sectional the following information on the specified key operation and the alarm: "The device is now entering the defibrillating mode, so if you are an unauthorized person, please do not enter that mode and please press key C to exit, otherwise a life risk will be caused. If you are an authorized person, please successively press the two keys A and B in sequence, to enter the defibrillating mode".

The operator makes a corresponding operation on the keys in the operation section 13 to determine whether to enter or to exit the selected function mode, after obtaining the information on the specified key operation and the alarm from the presentation section 11.

At step S30, after the operator makes a corresponding operation on the keys in the operation section 13, the control section 15 receives a key operation of the operator from the operation section 13.

At step S40, the control section 15 determines whether the received key operation of the operator is the same as the specified key operation indicating that the operator exits the selected operation mode.

When the determining result is yes, at step S70, the control section 15 does not start the selected function mode, and then the procedure ends.

When the determining result is no, at step S50, the control section 15 further determines whether the received key operation of the operator is identical to the specified key operation indicating that the operator enters the selected function mode.

When the further determining result is yes, at step S60, the control section 15 starts the selected function mode.

When the further determining result is no, the procedure returns to step S20 to continuously indicate the information on the specified key operation for entering or exiting the selected function mode and the information on the alarm.

It can be seen from the above embodiment that the invention has the following advantageous effect compared to the prior art. Firstly, when the operator selects to use a high risky function mode such as defibrillation, pacing and the like, the operator is required to make a specified key operation to determine whether to enter the selected function mode, and is alarmed of the risk caused by entering the function mode, so that the operator will not easily enter the high risky function mode, and will not forget the password when needing to use the high risky function mode such as defibrillation, pacing and the like urgently, which makes the high risky function of a defibrillator/monitor not be used casually while facilitates the use of the operator and avoids the delay of an rescue to a patient in emergency. Secondly, in the above embodiment of the invention, the specified key operation for determining to enter a high risky function mode may be a combined operation of two or more than two keys, and the two or more than two keys are not adjacent keys, so as to effectively avoid misoperation and further protect the high risky function modes of the defibrillator/monitor.

It's understood by those skilled in this art that although the above embodiment takes the defibrillator/monitor as an example to illustrate the invention, the invention is not limited to the defibrillator/monitor. In fact, the invention can be applied to other medical devices.

In addition, it's understood by those skilled in this art that although in the above embodiment the function modes that need protection are high risky function modes, the invention is not limited to that. In fact, in other embodiments of the invention, the function modes that need protection may be other function modes that need protection because of specific reasons.

The method of the invention may be implemented by software as well as hardware and the combination of software and hardware.

Figure 3:
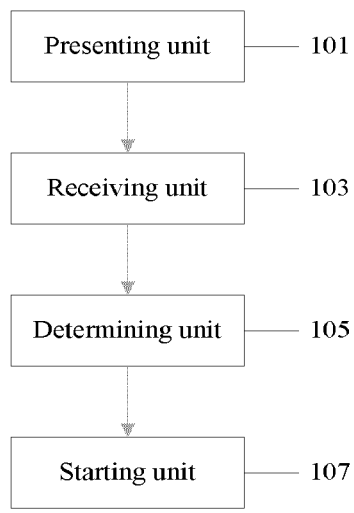
FIG. 3 is a block diagram of an apparatus for protecting a function mode of a defibrillator/monitor according to an embodiment of the invention.

FIG. 3 is a schematic diagram of an apparatus for protecting a function mode of a medical device according to an embodiment of the invention. As shown in FIG. 3, the apparatus 100 for protecting a function mode of a medical device comprises: a presenting unit 101, for when an operator selects to use a function mode that needs protection in the medical device, presenting the operator information on a specified operation for entering the selected function mode; a receiving unit 103, for receiving an operation of the operator; a determining unit 105, for determining whether the received operation of the operator is identical to the specified operation; and a starting unit 107, for starting the selected function mode when the determining result is confirmative.

Wherein, the specified operation is an operation of a single key or a combined operation of more than one key, the more than one key are not adjacent keys. The medical device includes a defibrillator/monitor. The function mode that needs protection includes a high risk function mode.

It should be appreciated by those skilled in this art that various changes and modifications may be made to the disclosed method and apparatus for protecting a function mode of a medical device without departing from the substance of this invention, therefore, the scope of this invention is defined by the appended claims.

What is claimed is:

1. A medical device capable of operating as a defibrillator or as a patient monitor, the medical device comprising:
   a presentation section configured to present information to an operator;
   an operation section configured to receive a key operation from an operator;
   a monitor section configured to be coupled with a patient so as to monitor a parameter of the patient when the medical device is operated as a patient monitor;
   an execution section configured to be coupled with a patient so as to execute defibrillation of the patient; and
   a control section in communication with each of the presentation section, the operation section, the monitor section, and the execution section, wherein the control section is configured to:
      control the presentation section when an operator selects to use the medical device in a defibrillating mode so as to present to the operator a specified key operation that is necessary for entry into the defibrillating mode;

determine whether a key operation received via the operation section is identical to the specified key operation;

control the executing section to start the defibrillating mode when it is determined that the key operation received via the operation section is identical to the specified key operation;

control the presentation section so as to present an additional key operation that is different from the specified key operation;

determine whether a key operation received via the operation section is identical to the additional key operation; and end a protecting procedure without starting the defibrillating mode if it is determined that the key operation received via the operation section is identical to the additional key operation.

2. The medical device according to claim 1, wherein the control section is configured to control the presentation section to continuously present both the specified key operation and the additional key operation until the control section determines that a key operation received via the operation section is identical to either the specified key operation or the additional key operation.

3. The medical device according to claim 1, wherein, when the control section controls the presentation section so as to present to the operator the specified key operation, the control section sends information to the presentation section such that the specified key operation is displayed as text.

4. The medical device according to claim 1, wherein the presentation section is configured to present a specified key operation that is an operation of a single key or a combined operation of more than one key.

5. The medical device according to claim 4, wherein the presentation section is configured to present a combined operation of more than one key that is performed on keys that are not adjacent to each other.

6. The medical device according to claim 1, wherein the presentation section is configured to present the specified key operation in conjunction with an alarm.

\* \* \* \* \*